US005785052A

United States Patent [19]
Johnson

[11] Patent Number: 5,785,052
[45] Date of Patent: Jul. 28, 1998

[54] VERSATILE DISPOSABLE FILM PROTECTIVE MASK

[76] Inventor: Joseph T. Johnson, 8028 Regent Park La., Charlotte, N.C. 28210

[21] Appl. No.: 379,021

[22] Filed: Jan. 27, 1995

[51] Int. Cl.$^6$ ................................................. H61F 6/06
[52] U.S. Cl. ........................ 128/830; 128/857; 128/859
[58] Field of Search ................................. 128/857, 859, 128/830

[56] References Cited

U.S. PATENT DOCUMENTS

| | | | |
|---|---|---|---|
| 4,875,490 | 10/1989 | Quiroz | 128/830 |
| 4,967,767 | 11/1990 | Harris et al. | 128/830 X |
| 4,981,147 | 1/1991 | Barnett | 128/842 |
| 4,993,431 | 2/1991 | Reddy | 128/830 |
| 5,016,649 | 5/1991 | Johnson | 128/859 |
| 5,113,873 | 5/1992 | Boarman | 128/830 |
| 5,146,930 | 9/1992 | Richardson et al. | 128/830 |
| 5,181,527 | 1/1993 | Dorsey et al. | 128/830 |
| 5,269,320 | 12/1993 | Hunnicutt | 128/830 |
| 5,413,117 | 5/1995 | Wills | 128/830 |

*Primary Examiner*—Max Hindenburg
*Attorney, Agent, or Firm*—Christopher C. Dremann

[57] ABSTRACT

A versatile disposable film protective mask includes an outlined boundary, a top pair of primary film strings, two top pairs of secondary film strings/ear loops, a bottom pair of primary film strings, a well-defined chin guard having chin guard receptors, jaw webs, cheek webs, an oral cavity web having oral cavity receptors and a reversible half-oval shaped flaccid oral cavity pouch. In a preferred embodiment, the versatile disposable film protective mask further includes a thin lining for those who are allergic to the film and to absorb liquids, i.e. saliva and/or perspiration produced by the wearer of the mask. The versatile disposable film protective mask can also be employed as a resuscitation mask, a dental dam, a male G-string flaccid pouch with a disposable film flaccid pouch harness or a female G-string flaccid pouch with a disposable film flaccid pouch harness. The versatile disposable film protective mask is employable for protecting the wearer against oral and genital infections with communicable diseases including viral diseases such as Human Immunodeficiency Virus (HIV) which has been known to lead to the development of Acquired Immunodeficiency Syndrome (AIDS). The mask is also employable for protecting the wearer against other oral and genital infections and Sexually Transmitted Diseases (STD's).

18 Claims, 11 Drawing Sheets

+  =

VERSATILE DISPOSABLE FILM PROTECTIVE MASK

FIELD OF THE INVENTION

This invention relates to a versatile disposable film protective mask (also referred to as the film mask, protective mask, or mask) that is designed and constructed to allow the mandible (jawbone), lips, and oral cavity to open as wide as necessary, without the mandible, lips, and oral cavity being restricted during the process. In addition, for those who are allergic to the film, the mask has a disposable thin lining that can be worn between the wearer's lower face and the film mask to help reduce the probability of an allergic reaction to the film material. Furthermore, the thin lining can also be used to absorb liquids, i.e., saliva and/or perspiration produced by the wearer of the film mask. This versatile disposable film protective mask is designed and constructed to operate in harmony and sequence with the mandible, lips, and outside and inside of the oral cavity of the wearer.

This invention is a versatile disposable film protective mask that can be worn by a male or female. This invention is a versatile disposable film protective mask that is employable for protecting the wearer against oral infections and communicable diseases, including viral diseases such as Human Immunodeficiency Virus (HIV) which has been known to lead to the development of Acquired Immunodeficiency Syndrome (AIDS). The wearer of this versatile disposable film protective mask can also be protected against other oral infections and oral Sexually Transmitted Diseases (STD's) like Herpes, Syphilis, Gonorrhea, Hepatitis-B, Chlamydia, Mononucleosis, and a host of other oral diseases. To date, no protective mask for the lower face has been designed and constructed to operate in harmony and sequence with the mandible, lips, and outside and inside of the oral cavity of the wearer.

BACKGROUND OF THE INVENTION

The public has become so fearful of contracting HIV/AIDS and other STD's that it has been buying and using a variety of devices in an attempt to serve its needs. Until now, there has not been a protective mask for the lower face that is designed, constructed, and capable of effectively alleviating the aforementioned public health concerns. This versatile disposable film protective mask is designed and constructed to be capable of alleviating these public health concerns. For example, this protective mask will simplify the process for covering and protecting the outside and inside of the oral cavity when dentists isolate and repair damaged teeth. Currently, dentists are using a 5×5 or 6×6 square piece of latex (known as a dental dam) to cover and protect the outside and inside of the oral cavity when repairing damaged teeth. A pouch is formed inside the oral cavity by clamping the center of the square piece of latex to the back teeth. A large plastic or metal frame is then placed in front of the face and the oral cavity. Next, the sides and corners of the square piece of latex are pulled forward and outward and mounted on the sides of the plastic or metal frame to hold the sides and corners of the square piece of latex in place and to secure the dental dam on the lower face of the wearer. This is a complicated procedure. One of the many functions of this protective mask is to replace the current dental dam, the plastic frame, and the metal frames. This protective mask is designed and constructed with a reversible half-oval shaped flaccid cavity pouch (also referred as the flaccid pouch or pouch) with an oral cavity web between it that conforms to the outside and inside of the wearer's oral cavity. In addition, the body of this protective mask has two types of webs (a jaw web and a cheek web) that will operate in harmony and sequence with the mandible (jawbone) allowing the dentist to open the wearer's oral cavity as wide as necessary. In addition, this protective mask has a top pair and bottom pair of primary film strings to secure the mask on the wearer's face, making it easier for the dentist to put the mask on and take it off the wearer's face. The flaccid pouch of this protective mask is compatible with the current equipment used to mark, clamp, and hold the current dental dam inside the oral cavity.

Protective masks for the face are of a crowded field which is mature and contains many patented inventions. However, no mask for the lower face is as versatile as this invention.

The Center for Disease Control (CDC) has added a response for callers who inquire about barrier methods for oral sex on their caller AIDS and STD's Hot Lines. The CDC currently suggests that a latex condom be used for oral sex. The CDC has stated that there are no devices specifically manufactured for oral sex. The applicant is aware of only three patented protective masks designed for oral sex:

THE FIRST: Rubin's oral sex protective mask, U.S. patent issued on Mar. 28, 1989, U.S. Pat. No. 4,815,456.

THE SECOND: Harding's oral sex protective mask, U.S. patent issued on Aug. 21, 1990, U.S. Pat. No. 4,949,731.

THE THIRD: Esqueda's oral sex protective mask, U.S. patent issued on Dec. 04, 1990, U.S. Pat. No. 4,974,605.

These three oral sex protective masks are limited in scope. All three masks are exclusively designed and constructed to perform only two of the ten facets of oral sex. Further, they are designed and constructed to allow the human tongue to perform only six of the basic tongue movements of oral sex.

Rubin's mask is restricted in scope because it provides only some margin of isolation of the lips, mouth, and tongue of the wearer. Rubin's mask is made of latex, generally flat, uniform in thickness, and rectangular in shape. The dimensions of the rectangular shaped configuration variably have a range of 8 to 15 inches in length and 2 to 5 inches in width. The protuberance diametral base and conical protuberance is in the approximate center of the rectangular mask (between it's two ear ends and it's two side ends) to receive and accommodate the human tongue. In order for the rectangular mask to provide a snug fit, it must be stretched around the ears and across the mouth of the wearer. The dimensions of the mask length should be smaller than the average human head from the back of the average human ears around the front of the face across the wearer's mouth area.

This brief description of the Rubin oral sex protective mask clearly states its employment, design, construction, restrictions, and limitations in scope, which are as follows:

1. It is designed and constructed to perform only two of the ten facets of oral sex.
2. The lips, the mandible, and the opening of the oral cavity are restricted by the design and construction of the Rubin mask.
3. The Rubin mask does not have the three webs (jaw, cheek, and oral cavity webs) that allow the mask to operate in harmony and sequence with the oral cavity, mandible, and lower face of the wearer.
4. The Rubin mask covers only a small portion of the wearer's cheeks.
5. The Rubin mask does not have a well-defined chin guard to cover the chin and the bottom of the mandible, with a cross section of pressure applied to it by a group of primary and secondary film strings that allow the mask to operate in harmony and sequence with the lower face of the wearer.

6. The Rubin mask does not have a well-defined chin guard (available with chin guard receptors).
7. The Rubin mask is not readily adjustable for a comfortable fit for a variety of wearers because the mask is secured on the lower face by small ear holes which are not adjustable. Therefore, several sizes would have to be made for the purchasing public. Further, it does not have a top pair of adjustable primary film strings nor a bottom pair of adjustable primary film strings that are uninterrupted components of the mask. The small ear holes cannot channel and disseminate the amount of pressure needed to allow the mask to operate in harmony and sequence with the wearer's lower face.
8. The uniform thickness of the Rubin mask imposes some major problems, i.e., if it is thin, the ear holes may rip or tear when it is stretched across the wearer's lower face or they can dig into the back of the wearer's ears making it very uncomfortable for the wearer of the mask. The thicker the uniform latex of the mask becomes the more flexibility the mask loses and the conical protuberance loses its pliability to the wearer of the mask.
9. The opening of the base of the Rubin mask will not allow the wearer's oral cavity to open wide enough for the large round disk that is commonly used during mouth-to-mouth resuscitation.
10. The opening of the base of the Rubin mask will not allow the wearer's oral cavity to open wide enough to be employed as a dental dam.
11. The opening of the base of the Rubin mask will not allow the wearer's oral cavity to open wide.
12. The Rubin mask does not have a disposable thin lining with outlined boundaries, jaw webs, cheek webs and a well-defined chin guard for those who are allergic to the film material that is also capable of absorbing liquids, i.e., saliva and/or perspiration produced by the wearer of the mask.
13. The opening of the base of the Rubin mask and the method used to secure the mask will not allow the mask to be employed as a male G-string flaccid pouch.
14. The opening of the base of the Rubin mask and the method used to secure the mask will not allow the mask to be employed as a female G-string flaccid pouch.

Harding's oral sex protective mask is likewise restricted in scope. It is designed and constructed to provide only a small margin of isolation for the lips, mouth and tongue of the wearer. Harding's entire mask is a mold-injected, shaped piece of rubber or synthetic flexible material that is rigid enough to maintain at all times the shape of the human lips, the tubular oral cavity insert, and the tongue protuberance. The configuration of the Harding mask is designed and constructed to cover only the wearer's lips. In addition, the portion of the Harding mask that goes into the wearer's oral cavity is tubular-shaped and has a tongue shaped molded protuberance at the bottom of the tubular oral cavity portion to receive the tongue. The mask is secured on the wearer's lower face by using adhesive or a stretchable elastic band.

This brief description of the Harding oral sex protective mask clearly states its employment, design, construction, restrictions, and limitations in scope, which are as follows:
1. The Harding mask is designed and constructed to perform only two of the ten facets of oral sex.
2. The opening of the Harding mask oral cavity will not allow the wearer to perform the other facets of oral sex.
3. The Harding mask does not have the three webs (jaw, cheek, and oral cavity webs) that allow the mask to operate in harmony and sequence with the lower face of the wearer.
4. The Harding mask does not have a well-defined chin guard to cover the chin and the bottom of the mandible, with a cross section of pressure applied to it by a group of primary and secondary film strings that allows the mask to operate in harmony and sequence with the lower face of the wearer.
5. The harding mask does not have a well-defined chin guard (available with chin guard receptors).
6. The Harding mask is not readily adjustable for a comfortable fit for a variety of wearers. Several sizes would have to be made for the purchasing public. It does not have a top pair of adjustable primary film strings nor a bottom pair of adjustable primary film strings that are uninterrupted components of the mask and that can channel and disseminate the amount of pressure needed to allow the mask to operate in harmony and sequence with the wearer's lower face.
7. Because of the thickness of the material and the design of the Harding mask, the oral cavity of the wearer is always in the wide open position. The oral cavity can never close as long as the wearer has the Harding mask on because its tubular shape is not self-adjusting.
8. The Harding mask is very uncomfortable for the wearer to keep in his oral cavity for any given length of time because the tubular insert forces the wearer's oral cavity to remain in the wide open position at all times.
9. The opening of the base of the Harding mask will not allow the wearer's oral cavity to open wide enough for the large round disk that is commonly used during mouth-to-mouth resuscitation.
10. The opening of the base, the materials used, and the design of the Harding mask will not allow the wearer's oral cavity to open wide enough to be employed as a dental dam. In addition, the tongue protuberance would be in the dentist's way while repairing the patient's teeth.
11. The opening of the base of the Harding mask will not allow the wearer's oral cavity to open wide.
12. The Harding mask does not have a disposable thin lining with outlined boundaries, jaw webs, cheek webs, and a well-defined chin guard for those who are allergic to the film material that is also capable of absorbing liquids, i.e., saliva and/or perspiration produced by the wearer of the mask.
13. The opening of the base, materials used, and the method used to secure the Harding mask will not allow the mask to be employed as a male G-string flaccid pouch.
14. The opening of the base, materials used, and the method used to secure the Harding mask will not allow the mask to be employed as a female G-string flaccid pouch.

The Esqueda oral sex protective mask provides more facial coverage than the Rubin or the Harding mask. In addition to covering the lips, mouth, and the tongue, it also covers the entire nose, cheeks, and the mandible of the wearer. Although it provides more facial coverage, the design and construction of the Esqueda mask are still limited in scope. In order for the wearer to breathe while wearing the mask, it is equipped with two nasal tubes for the nose. For the latex mask to provide adequate contact with the upper front part of the face (which crosses the bridge of the nose), the chin portion, and the side boundaries of the mask may be provided with a thicker edge and/or wire or similar insert. The insert may be of a formable material, such as a soft metal alloy, so as to be able to be conformed to the specific shape of an individual face. The mask has a protuberance to accommodate the tongue, and it can be held closely to the face with elastic straps, ties, bands with buckles, or any other convenient and well-known means of attaching a mask to the face.

This brief description of the Esqueda oral sex protective mask clearly states its employment, design, construction, restrictions, and limitations in scope, which are as follows:

1. The Esqueda mask is designed and constructed to perform only two of the ten facets of oral sex.
2. The oral cavity, lips, and the mandible are restricted by the design and construction of the Esqueda mask. They cannot open wide enough to perform the other facets of oral sex. If the wearer attempted to do so, the mask would become displaced and the two nasal tubes would come out of the nasal passage, prohibiting the wearer from breathing.
3. The bridge of the nose, the side boundaries, and the chin sections of the Esqueda mask are made of thick latex and/or wire or soft metal alloy.
4. The Esqueda mask does not have the three webs (jaw, cheek, and oral cavity webs) that allow the mask to operate in harmony and sequence with the outside and inside of the oral cavity, lips, and lower face of the wearer.
5. The Esqueda mask does not have a well-defined chin guard to cover the chin and the bottom of the mandible, with a cross section of pressure applied to it by a group of primary and secondary film strings that allows the mask to operate in harmony and sequence with the lower face of the wearer.
6. The Esqueda mask does not have a well-defined chin guard (available with chin guard receptors).
7. The Esqueda mask is not readily adjustable for a comfortable fit for a variety of wearers because of the material used to design and construct the mask. The mask is mounted on wire, alloyed metal, and/or the outlined boundary of the mask is constructed of a thicker latex material in order to shape the mask to the wearer's face. Therefore, several sizes would have to be made for the purchasing public. It does not have a top pair of adjustable primary film strings nor a bottom pair of adjustable primary film strings that are uninterrupted components of the mask that can channel and disseminate the amount of pressure needed to allow the mask to operate in harmony and sequence with the wearer's lower face.
8. The tubes of the Esqueda mask in or in front of the nose would make it very difficult for the wearer to breath.
9. The opening of the base of the Esqueda mask will not allow the wearer's oral cavity to open wide enough for the large round disk that is commonly used during mouth-to-mouth resuscitation.
10. The opening of the base of the Esqueda mask will not allow the wearer's oral cavity to open wide enough to be employed as a dental dam.
11. The opening of the base of the Esqueda mask will not allow the wearer's oral cavity to open wide.
12. The Esqueda mask does not have a disposable thin lining with outlined boundaries jaw webs, cheek webs, and a well-defined chin guard for those who are allergic to the film material that is also capable of absorbing liquids, i.e., saliva and/or perspiration produced by the wearer of the mask.
13. The opening of the base and the design and construction of the Esqueda mask will not allow the mask to be employed as a male G-string flaccid pouch.
14. The opening of the base and the design and construction of the Esqueda mask will not allow the mask to be employed as a female G-string flaccid pouch.

SUMMARY OF THE INVENTION

The invention is a versatile disposable film protective mask (which begins under the nose of the wearer and ends under the wearer's mandible) that operates in harmony and sequence with the wearer's lips, mandible, and the outside and inside of the oral cavity to allow them to open wide and close without being restricted in any way. In addition, the mask may be provided with a disposable thin lining (which can be worn between the mask and the lower face of the wearer) that is configured like the body of the film mask with the jaw webs, cheek webs, and a well-defined chin guard. The thin lining is available for those who are allergic to the film material, and is also capable of absorbing liquids, i.e., saliva and/or perspiration produced by the wearer of the mask due to its harmony and sequence with the wearer's lips, mandible, and outside and inside of the oral cavity. The wearer of this current invention can perform the ten facets of oral sex. The mask can also be employed as a wide open mouth-to-mouth resuscitation mask, a wide open or closed oral cavity dental repair mask, a male G-string flaccid pouch or a female G-string flaccid pouch.

There are several objectives and advantages of the invention, which are as follows:

1. A mask that is held securely on the top portion of the wearer's lower face (beginning under the nose of the wearer) by a top pair of primary film tying strings;
    A. The top pair of primary and two pairs of secondary film strings are of a different texture than the body of the film protective mask to prevent ripping or tearing when they are tightened and to transmit the necessary pressure to the boundaries and center portion of the mask, which begins underneath the nose and covers the cheeks, chin, and mandible of the wearer.
    B. The top pair of primary film strings (which are tied at the back of the head, near the top back of the ears of the wearer) channel and transmit pressure to the boundaries and center portion of the mask. They create a cross-section of pressure on the well-defined chin guard of the mask by pulling the mask backwards and upwards on the lower face of the wearer. The secondary two pairs of film strings are pulled by the top pair of primary film strings. This pulling process (from the top pair of primary film strings) applies pressure against the secondary two pairs of film strings which likewise channel and transmit pressure to the boundaries and center portion of the mask.
2. A mask that is also held securely on the bottom portion of the wearer's lower face by a bottom second pair of primary tying film strings;
    A. The second pair of primary film strings are made of a different texture than the body of the film protective mask to prevent ripping or tearing when they are tightened just like the top pair of primary and two pairs of secondary film strings. The second pair extends from the bottom of the outlined boundary of the mask near the well-defined chin guard underneath the mandible and are tied behind the upper part of the wearer's neck.
    B. When the secondary pair of primary film strings are tied, they create and transmit a cross-section of pressure on the well-defined chin guard by pulling it backwards and downwards on the chin and mandible of the wearer.
    C. This additional channel of transmitted pressure on the well-defined chin guard (in conjunction with the first channel of pressure) allows the mask and boundaries of the mask to operate in harmony and sequence with the lower face muscles, mandible, lips, and oral cavity so that they can open wide and close without being restricted in the process.

3. A mask that has three moveable webs;
   A. The first pair of connecting webs are the jaw webs that are shaped like the greater than mathematical sign {>}, which has a narrow groove or pleated fold between it when in the closed position.
   B. The jaw webs are on the sides of the mask.
   C. The purpose and function of the jaw webs are to reduce the stress that is created on the sides of the mask when the mandible and oral cavity begin to open wide, with the help of the groove/pleated fold between the jaw webs, which opens into a wider jaw web position. If the jaw webs were eliminated, the level of stress would be so great that it would cause the mask to become displaced when the mandible and oral cavity began to open wide.
   D. The second pair of webs are the cheek webs which are located in the approximate center of the jaw webs, located on each of the front/sides of the cheeks. When closed the cheek webs are in a narrow pleated fold or groove position.
   E. The purpose and function of the cheek webs are to reduce the stress that is created on the front/sides of the mask when the mandible, lips, and oral cavity begin to open wide, with the help of the groove/pleated fold between the cheek webs, which opens into a wider cheek web position. If the cheek webs were eliminated, the level of stress would be so great that it would cause the mask to become displaced when the mandible and oral cavity began to open wide.
   F. The third web is the oral cavity web, which is a part of and connected to the cheek webs. The oral cavity web is in the approximate center of the reversible half-oval shaped flaccid cavity pouch. When closed, the oral cavity web is also in a narrow pleated fold or groove position.
   G. The purpose and function of the oral cavity web is four-fold. First, it will reduce the stress created on the front/center of the mask when the mandible, lips, and oral cavity begin to open wide; second, it will increase the width and length of the reversible flaccid pouch when it's narrow pleated fold or groove opens into a wider web; third, it is capable of storing a lubricant in it's pleated/grooved fold to make the reversible flaccid pouch self-lubricating; and fourth, the groove/pleated fold of extra film material may also have oral cavity receptors on it (which are receptacle protuberances formed as ridges, disks, bulges, tentacles, or knobs). The oral cavity receptors also enhance and specialize in providing additional stimuli to the receiver.
4. A mask that has a reversible half-oval shaped flaccid cavity pouch, also referred to as reversible flaccid pouch or flaccid pouch;
   A. When closed the reversible half-oval flaccid cavity pouch has a medium size half-oval shaped component which is located in front of the wearer's lips, which begins directly under the nose bone at the top of the wearer's maxilla and ends near the mental foramen. The oral cavity web is in the approximate center of the reversible half-oval shaped flaccid cavity pouch.
   B. The purpose and function of the reversible flaccid pouch is to protect and operate in harmony and sequence with the front outside and inside of the oral cavity of the wearer. This component, with the help of the oral cavity web, can increase in size from a medium half-oval shaped component to a large half-circular shaped component without displacing the outlined boundaries of the mask.

The purpose and functions of the three webs (jaw, cheek, and oral cavity webs) are to reduce the stress that is created on the sides, center, and front of the mask when the mandible, oral cavity, and lips begin to open wide. The three webs reduce the stress that would otherwise displace the mask when it is being employed by pulling the top portion of the mask outlined boundary down into the oral cavity of the wearer, or making it difficult for the wearer to open his/her oral cavity wide. The purpose and function of the reversible flaccid pouch is to protect the outside and inside of the oral cavity and to reduce the stress that is created on the front of the mask when the mandible, oral cavity, and lips begin to open wide. When the stress points are reduced and alleviated, the film protective mask will stay in position by being held closely and securely on the wearer's lower face to operate in harmony and sequence with the mandible, the lips, and the oral cavity of the wearer without being displaced or restricted in movement.

The mask may be employed as:
1. A Resuscitation mask;
2. A Mask For Isolating Damaged Teeth (dental dam);
3. A Male G-string Flaccid Pouch; or
4. A Female G-string Flaccid Pouch.

Whether the mask is employed as a disposable protective lower face mask, a male G-string flaccid pouch, or a female G-string flaccid pouch, it is designed and constructed to act as an additional protective layer of skin for the wearer. It may also be provided with a disposable thin lining that is configured like the body of the film mask with the outlined boundaries, the jaw webs, the cheek webs, and a well-defined chin guard. This thin lining is available for those who are allergic to the film. It should be worn between the mask and the lower face of the wearer to reduce the allergic reaction to the film. The thin lining is also capable of absorbing liquids, i.e., saliva and/or perspiration produced by the wearer of the film mask. Additional objectives and advantages of the invention will become apparent from a consideration of the following description and accompanying drawings.

DETAILED DESCRIPTION OF THE PREFERRED EMBODIMENTS

Figure 1:
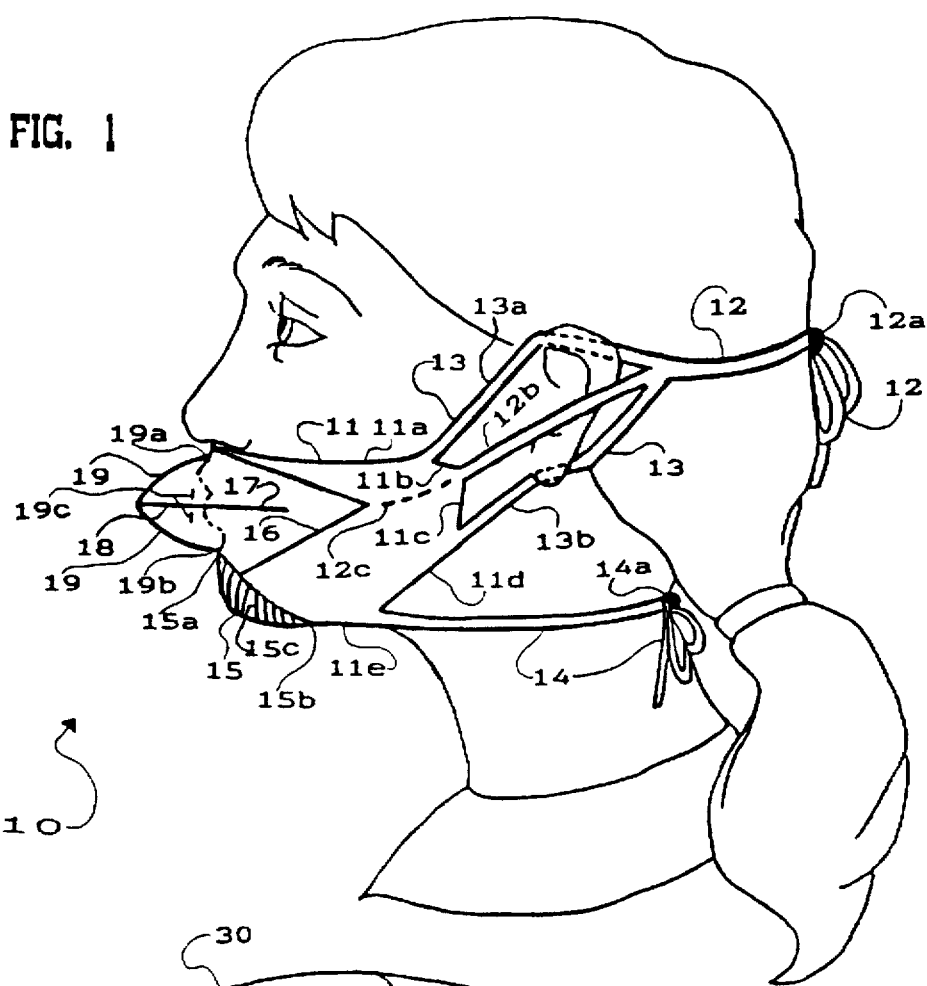
FIG. 1 is a left side-view of the protective mask with the oral cavity and webs in the closed position and with the reversible flaccid pouch in front of and on the outside of the oral cavity.

The present invention will be described more fully hereafter. This invented versatile disposable film protective mask 10 is a dipped/molded uninterrupted liquid latex or liquid polyurethane or any other liquid virus impermeable film material, that will help prevent the wearer from coming in contact with communicable diseases.

The mold for this mask 10 is shaped like a human beings lower face, beginning under the nose, with a well-defined chin 15 shaped bottom portion of the mold. The well-defined chin portion 15 also has a shallow top side 15a and bottom side 15b outlined groove formed in the lower front section of the body of the mold, to further define the chin portion 15 of the mold. In addition, the mold for the mask has a medium half-oval shaped extended portion 19, just above the top outlined groove 15a of the well-defined chin 15 configuration of the mold, to form the reversible flaccid cavity pouch 19. The medium half-oval shaped extended portion 19 has an oval horizontal deep groove or pleat formed in its approximate center, to define the oral cavity web 18/18a of the mold.

Next, the body of the mold for the mask has one deep groove or pleat formed in each front/side of the mold, partially connecting with the oral cavity web 18/18a (shaped like the minus mathematical sign); positioned in the approximate center of the jaw webs 16, to define the cheek webs 17/17a of the mold. Further, the mold for the mask has one deep groove or pleat (shaped like the greater than mathematical sign) formed in each side of the mold. The top ends of the greater than sign unite just above the medium half-oval shaped extended portion 19 of the mold. The bottom ends of the greater than sign are connected to the side outlined groove 15a/15b of the well-defined chin 15 configuration of the mold, to define the jaw webs 16/16a of the mold.

The strategically shaped and formed mold of the mask is then dipped into a warm liquid latex or polyurethane or any other liquid virus impermeable film compound to form a coating over the mold. After dipping and cooling, the liquid is then transformed into a solid film. Lastly, the film mask 10 is pulled off the mold and the outlined boundary 11, top primary 12, top secondary 13, and 10 bottom primary 14 film strings are strategically cut to achieve the totality of this invented mask 10.

In order for one to obtain a complete understanding of the adjustable, stationary, and movable components of this mask, their descriptions and operations will be explained separately, so that one can appreciate the individual contributions each component contributes to this invented versatile disposable film protective mask 10 as a whole. With references to the accompanying drawings in which preferred embodiments of the invention are shown, it is to be understood at the commencement of the descriptions and operational declarations of this mask 10, that persons of skill in the appropriate art may modify the invention described herein while still achieving the favorable results of this invention. Accordingly, the descriptions and operations of this invented versatile disposable film protective mask 10 and it's components, which follow, are to be understood as being broad teaching disclosure directed to persons of skill in the appropriate art and not as limiting upon the present invention.

I. OUTLINE BOUNDARIES OF THE MASK—DESCRIPTION

Figure 6:
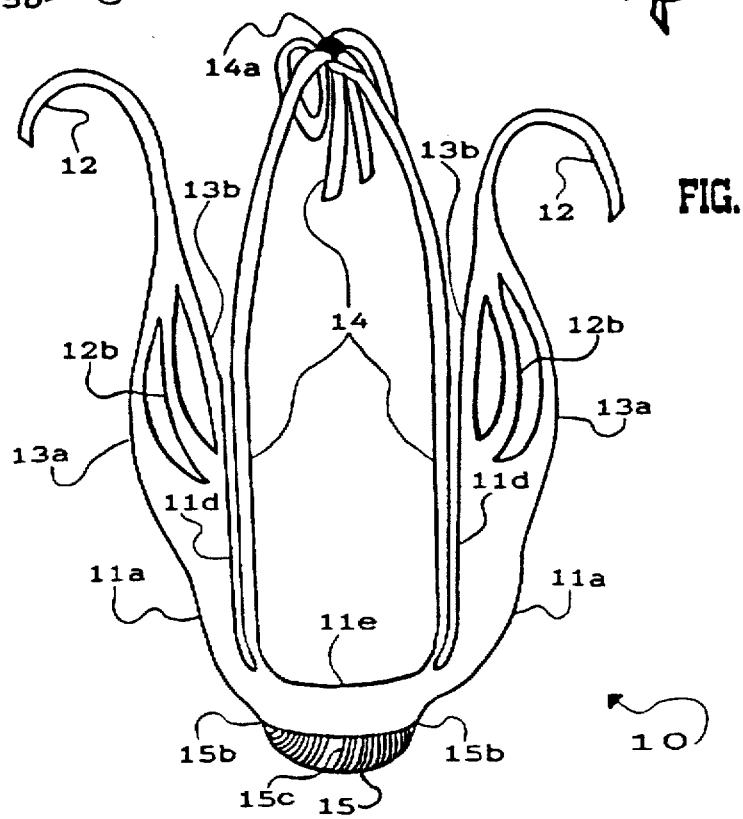
FIG. 6 is an isolated bottom-view of the protective mask indicating the outlined boundaries, top and bottom pairs of primary film strings, top pairs of secondary film strings, the well-defined chin guard and the chin guard receptors.

Referring now more particularly to the accompanying drawings, a versatile disposable film protective mask 10 as contemplated by this invention is shown in the side views of FIGS. 1, 1A, 2, 2A, 3, 3A, 4, 4A, and 5, and the bottom-view of FIG. 6. The outlined boundaries 11 of the 40 mask are as follows: The top portion of the mask is 11a, which begins underneath the nose bone 30b, continues along the top middle portion of the maxilla 30c, along side the malar bone 30a, provides substantial cheek coverage, partial maxilla 30d coverage on both sides, and partial coverage of the bottom portion of the mandible 40, of the face from 11a through 11e. The mask center side boundaries, the bottom end of 11b and the top end of 11c flow uninterrupted to form the top primary pair of film strings 12, which are of a different texture than the body of the film protective mask to prevent ripping or tearing when they are tightened at 12a and which are strategically cut out of the side portion of the mask 10 to ensure a continuation of the outlined boundary 11 of the mask.

The mask top side end 11a and the top of 11b of the outlined boundaries flow uninterrupted to form 13a the film's top pair of secondary strings which flows uninterrupted into 12. The bottom portion of 11c and the top portion of 11d of the outlined boundary 11 flow uninterrupted to form 13b the film's bottom pair of secondary strings which flows uninterrupted into 12. When 13a and 13b unite with 12 together they form the ear loops 13, which are made of the same texture as the top pair of primary film strings 12 to also prevent ripping or tearing when the top pair of primary film strings 12 are tightened at 12a. The bottom portion of the outlined boundary of 11d and the back end of 11e flow together to form the bottom pair of primary film strings 14, which are likewise made of a different texture than the body of the film protective mask 10 to prevent ripping or tearing when they tighten at 14a and which are strategically cut out of the bottom portion of the mask to ensure a continuation of the outline boundary 11 of the mask 10.

The bottom portion 11e of the mask 10 is formed by a plurality of folded pleats (FIG. 1) of the film material. The well-defined chin guard 15 (shaped like a human's beings chin) begins at 15a and ends at 15b (the outlined boundaries of the well-defined chin guard 15 to give further definition and contour to the well-defined chin guard 15) where it flows uninterrupted into the outlined boundary of 11e. In addition, the well-defined chin guard 15 is available with chin guard receptors 15c, which are receptacle protuberances formed as ridges, disks, bulges, tentacles, or knobs on the well-defined chin guard 15.

II. OUTLINED BOUNDARIES OF THE MASK—OPERATIONS

1. When the top pair of primary film strings 12 are united and tightened at 12a, the pressure from them are channeled and disseminated throughout the body of the mask 12c and the outlined boundaries 11 (11a, 11b, 11c, 11d, and 11e) of the mask 10 in the following ways:

A. The pressure is channeled and disseminated throughout the top 11a, center 11b/11c, sides 11d, and bottom 11e portions of the outlined boundaries 11 of the mask 10, from the top secondary film strings 13 (13a and 13b). The pressure from 13a is channeled and disseminated throughout the top portion 11a of the mask outlined boundary 11 which applies pressure on the top center of the maxilla 30c and along side the bottom of the malar bone 30a (refer to FIG. 1A), to properly pull back, stabilize, and secure the top portion 11a of the outlined boundary 11 to the upper lower face of the wearer. The pressure from 13b is channeled and disseminated throughout the side portions 11d of the mask outlined boundary 11 which applies pressure on the side of the mandible 40 and the well-defined chin guard 15 to properly pull back, stabilize, and secure the side portions 11d of the outlined boundary 11 and the well-defined chin guard 15 of the mask 10, to the side lower face of the wearer.

B. The pressure from the top pair of primary film strings 12 (12a and 12b) is also channeled and disseminated throughout the center 11b/11c of the outlined boundary of 11 and continues to be transmitted into the body of the mask 12c (as indicated by the hidden lines on the side of the mask 10) to prevent it from shifting when the mask 10 is being employed. The pressure continues to be transmitted throughout 12c until it reaches the well-defined chin guard 15. This pressure, in conjunction with 13b, will pull the well-defined chin guard 15 in the upper angled direction of the top pair of primary film strings 12. This upper angled position creates a cross-section of pressure that pulls back, stabilizes, and secures the well-defined chin guard 15 against the chin of the wearer when the mask 10 is being employed.

C. The two pairs of secondary film strings 13 primary functions are to channel pressure throughout the top and side boundaries 11a and 11d of the mask when 12a is tightened or loosened by the wearer. The two pairs of secondary film strings/ear loops 13 cannot be and are not employed to adjust the amount of pressure that is disseminated throughout the outlined boundaries 11. In addition to the two pairs of secondary film strings 13 aforementioned functions, the two pairs of secondary film strings 13 are also employed as safety film strings in case the wearer of the mask 10 does not tighten the top pair of primary film strings 12 at 12a in the proper manner, so that the top center portion of the mask boundary 11a will not come off the wearer's face or slide down into the wearer's oral cavity when the reversible flaccid pouch is in the wide opened position.

2. When the bottom pair of primary film strings 14 (the adjustable components of the mask 10) are united and tightened at 14a, the pressure from them is channeled and disseminated throughout 14. This transmitted pressure is applied to the bottom 11e outlined boundary of 11 and the well-defined chin guard 15 of the mask 10 in the following ways:

A. The pressure transmitted at the bottom 11e outlined boundary of 11 flows into 15b, the end portion of the well-defined chin guard 15, thus creating a cross-section of pressure by pulling it back, stabilizing it, and securing the well-defined chin guard 15 against the chin of the wearer when the mask 10 is being employed.

B. The well-defined chin guard 15 has a cross-section of pressure that is channeled and disseminated throughout it. This cross-section of pressure allows the well-defined chin guard 15 to perform in harmony and sequence with the mandible 40 (which has a vast cross-section of muscles to allow it to open wide and close at will). Thus, the cross-section of pressure pulls back, stabilizes, and secures the well-defined chin guard 15 against the chin of the wearer.

III. THE THIN LINING—DESCRIPTIONS AND OPERATIONS

1. The Description

Figure 7:
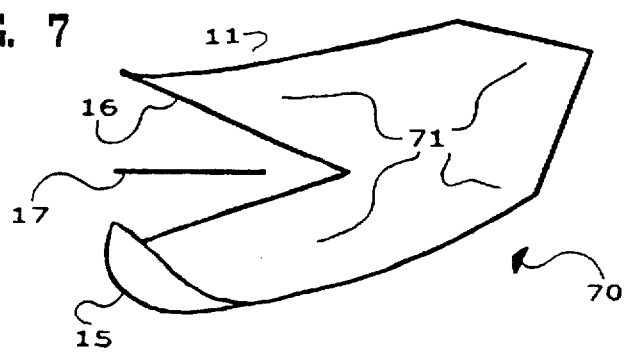
FIG. 7 is an isolated left side-view of the protective mask disposable thin lining for use by those who are allergic to the film, with outlined boundaries, cheek web, jaw web and well-defined chin guard.

FIG. 7 is a side-view of the disposable thin lining 70 that can be made of cotton or any other material that is capable of reducing the allergic reaction some wearers may have to the film material of the mask 10. The thin lining 70 may be worn between the wearer's lower face and the film protective mask. Like the mask 10, the body of the thin lining 70 is comprised of the outlined boundaries of 11, the well-defined chin guard 15, the jaw webs 16/16a, and the cheek webs 17/17a. Unlike the mask 10, the thin lining 70 does not have the secondary film strings 13, the top pair of primary film strings 12, or the bottom pair of primary film strings 14.

2. The Operation

The purpose of the disposable thin lining 70, FIG. 7, is to operate in harmony and sequence with the lower face and the film protective mask 10. The thin lining 70 may have, if necessary, an adhesive substance on the outside of it as indicated by 71 to prevent it from shifting or becoming displaced while being employed. The adhesive substance 71 will not obstruct, impede, retard, or hinder the operations of the jaw webs 16/16a and cheek webs 17/17a of the thin lining 70, or the webs of the film mask 10. The primary function of the thin lining 70 is to reduce the allergic reaction some wearers may have to the film material of the film protective mask 10. The thin lining 70 also absorbs liquids, i.e., saliva and/or perspiration, produced by the wearer of the mask 10.

IV. THE WEBS—DESCRIPTIONS AND OPERATIONS

This mask 10 which is made out of a film material, when worn closely to the lower face (beginning underneath the nose) of the wearer during employment, has the capability to expand when the lower face of the wearer applies a great amount of stress to the body and to the outlined boundary 11a of the mask 10. But, during this expansion process it would restrict the movement of the lips, mandible 40, and prevent the oral cavity 60 from opening to its fullest capacity. In turn, it would prevent the mask 10 from operating in harmony and sequence with the mandible 40, oral cavity 60, and the muscles of the lower face—thus, the outlined boundaries of 11 of the mask 10 would be so tight that the mask 10 would be very uncomfortable for the wearer. Furthermore, if the oral cavity were to open wide, the top center section 11a of the outlined boundary 11 would be pulled down into the wearer's oral cavity 60. That is why the webs are very important for this mask 10 to perform to its fullest capacity and operate in harmony and sequence with the lips, mandible 40, oral cavity 60, and the muscles of the lower face of the wearer.

Figure 8:
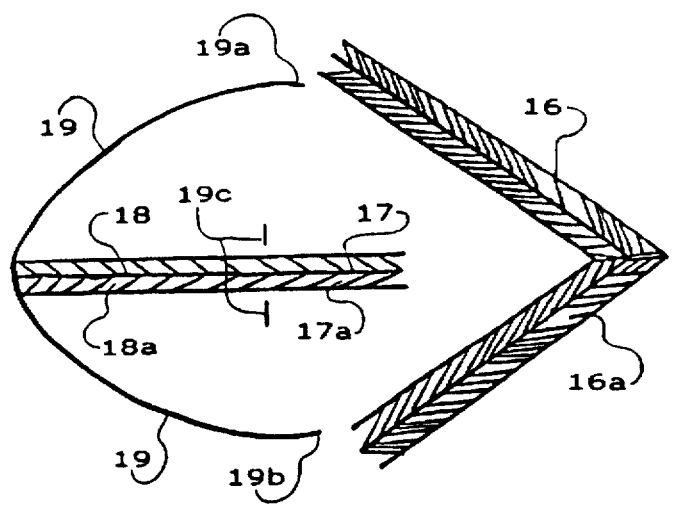
FIG. 8 is an isolated left side-view of the protective mask indicating the oral cavity web, cheek web and jaw web in the closed position and with the reversible flaccid pouch in front of and on the outside of the oral cavity.
Figure 9:
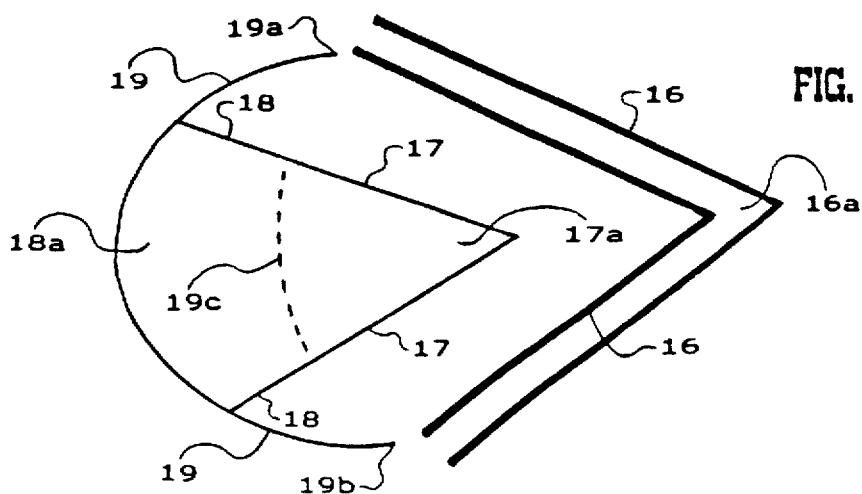
FIG. 9 is an isolated left side-view of the protective mask indicating the oral cavity web, cheek web and jaw web in the wide opened position and with the reversible flaccid pouch in front of and on the outside of the oral cavity.
Figure 10:
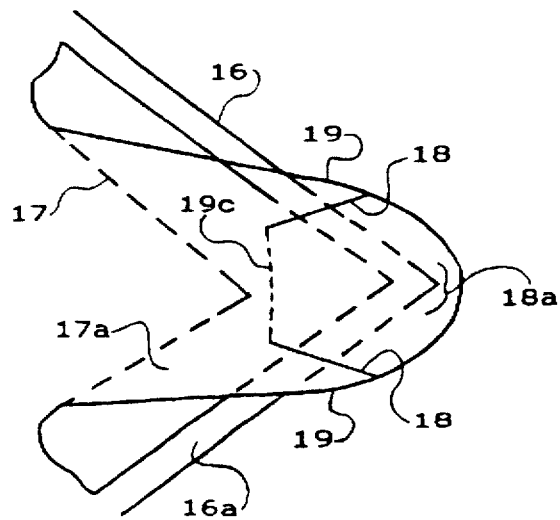
FIG. 10 is an isolated left side-view of the protective mask indicating the oral cavity web, cheek web and jaw web in the wide opened position and with the oral cavity web and the reversible half-oval shaped flaccid cavity pouch inside the oral cavity.

FIG. 8, FIG. 9, and FIG. 10 are side-view closeups of three of the movable components, the versatile disposable film protective mask 10 of FIG. 1, which are as follows:
1. The Jaw Webs
2. The Cheek Webs
3. The Oral Cavity Web 1. The Jaw Webs A. Description The jaw webs 16, when closed, have a narrow groove with a structure similar to the greater than mathematical sign {>} shape, as shown in FIG. 8. Located along the sides of the Maxilla 30d and the Mandible 40, the top portion of the jaw webs 16 is just below the front center of the top outlined boundary area 11a and the bottom portion of the jaw webs 16 connects with the well-defined chin-guard 15. The jaw webs 16 have a groove or pleated fold of extra film between its edges 16a.

B. Operation

The jaw webs 16 are provided to relieve and alleviate the great amount of stress that is created on the top outlined boundary 11a and the side body of the mask 10 when the mandible 40 begins the process of opening wide to expose the oral cavity 60. The mandible is the only movable bone connected to the skull 30, due to the Condyloid and Coronoid processes 40b. The jaw webs 16 will expand into a wider groove with the help of the groove or pleated fold of extra film material between its edges 16a to reduce the buildup of stress on the top outlined boundary 11a and the sides of the mask 10, as shown in FIG. 9. In turn, the top portion 11a of the outlined boundary 11 of the mask 10 will remain in its desired position during employment.

2. The Cheek Webs

A. Description

The cheek webs 17 form a narrow horizontal slit, i.e. {-} when in the closed position, and are located on the front/sides of the mask 10. As shown in FIG. 8, they are positioned directly between the narrow {>} shaped jaw webs 16. The cheek webs 17 have a groove or pleated fold of extra film between its edges 17a.

B. Operation

When the cheek webs 17 expand from a narrow horizontal slit, the groove or pleated fold of extra film between its edges 17a will expand into a wide {>} shaped web. This expansion takes place when the lips separate, the mandible (jawbone) 40 begins to drop, and the oral cavity 60 begins to open wide. Thus, the groove or pleated fold of extra film between its edges 17a greatly reduces the buildup of stress that is created on the top outlined boundary 11a and the front/sides of the mask 10 when the above process takes place, as shown in FIG. 9. In turn, the top portion 11a of the outlined boundary 11 of the mask 10 will remain in its desired position during employment.

3. The Oral Cavity Web

A. Description

The oral cavity web 18 partially connects to the cheek webs 17, which are separated by 19c. FIG. 10 depicts the separation of the cheek webs (17/17a) and the oral cavity web (18/18a), as indicated by the hidden lines. When in the closed position, the oral cavity web 18 will also have a narrow half-oval pleat or groove slit 18a, as shown in FIG. 8. In addition, the groove or pleated fold of extra film material 18a may also have oral cavity receptors 18b, as shown FIG. 4, on it which are receptacle protuberances formed as ridges, disks, bulges, tentacles, or knobs. The oral cavity web 18 is directly in front of the wearer's oral cavity 60 and is in the approximate center of the flaccid cavity pouch 19.

B. Operation

When the oral cavity web 18 expands from a narrow half-oval slit the extra film pleat or groove 18a will expand into a wide left parenthesis {(} shaped web, as shown in FIG. 9. This expansion takes place when the mandible 40 drops and the oral cavity 60 begins to open wide. This greatly reduces the buildup of stress that is created on the top outlined boundary 11a and the front portion of the mask 10. The oral cavity webs 18 with the help of the extra film pleat or groove 18a, which forms part of the pouch 19 that protects the outside and/or inside of the oral cavity, keeps the top portion 11a of the outlined boundary 11 in its desired position during employment.

V. THE REVERSIBLE FLACCID CAVITY POUCH—DESCRIPTION AND OPERATION

1. The reversible half-oval shaped flaccid cavity pouch 19.

A. Description

Figure 1A:
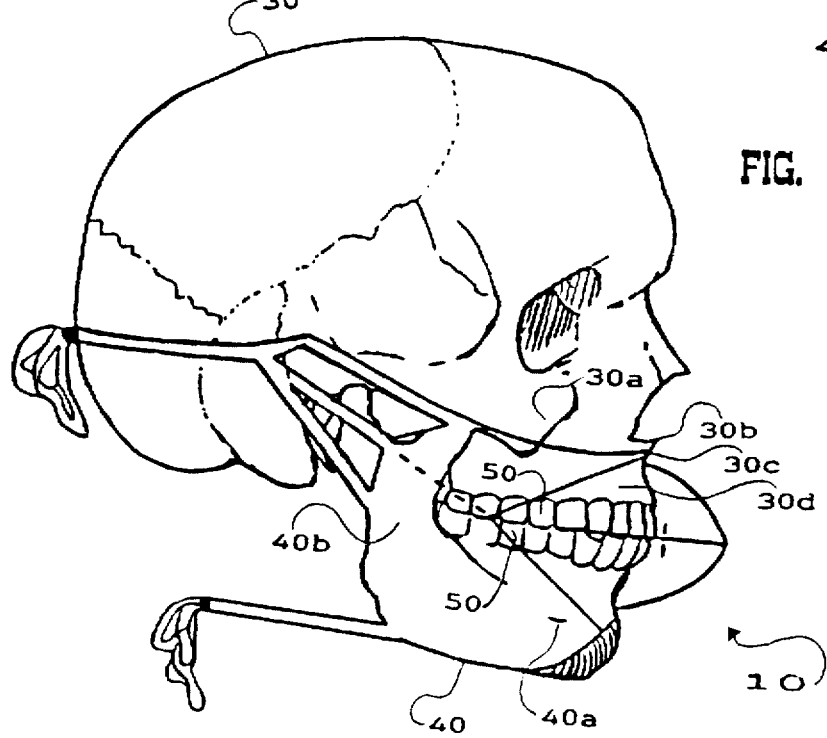
FIG. 1A is a right side-view of the protective mask indicating the position of the mandible when the oral cavity and webs are in the closed position and with the reversible flaccid pouch in front of and on the outside of the oral cavity.
Figure 2:
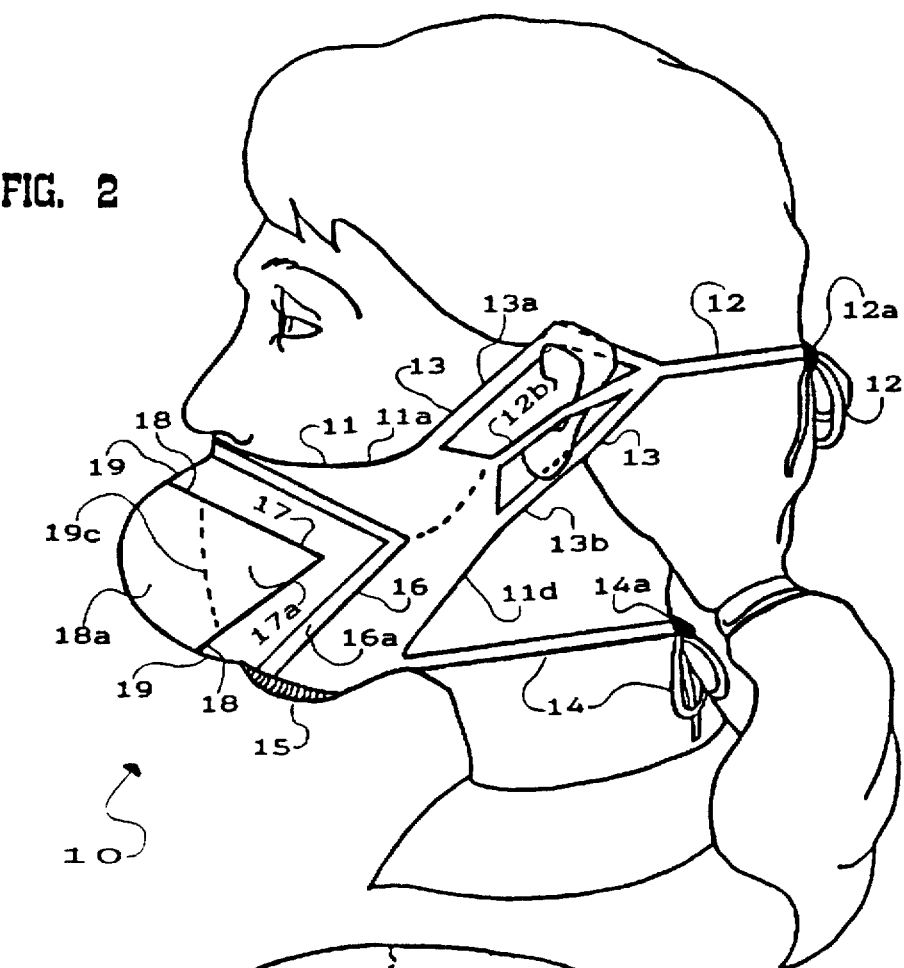
FIG. 2 is a left side-view of the protective mask, with the oral cavity and webs in the wide opened position and with the reversible flaccid pouch in front of and on the outside of the oral cavity.
Figure 2A:
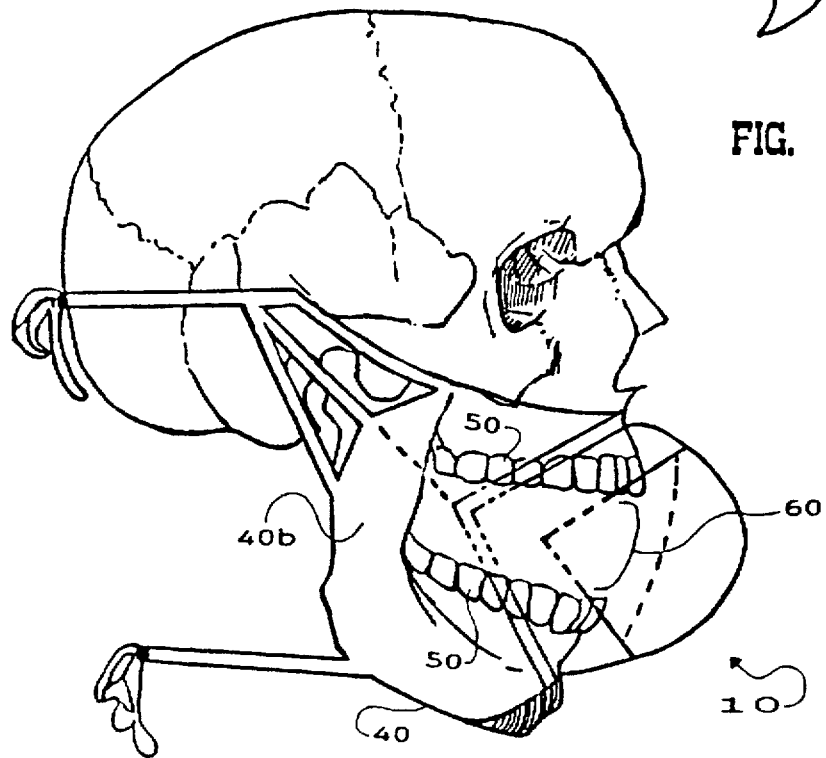
FIG. 2A is a right side-view of the protective mask indicating the position of the mandible when the oral cavity and webs are in the wide opened position and with the reversible flaccid pouch in front of and on the outside of the oral cavity.
Figure 3:
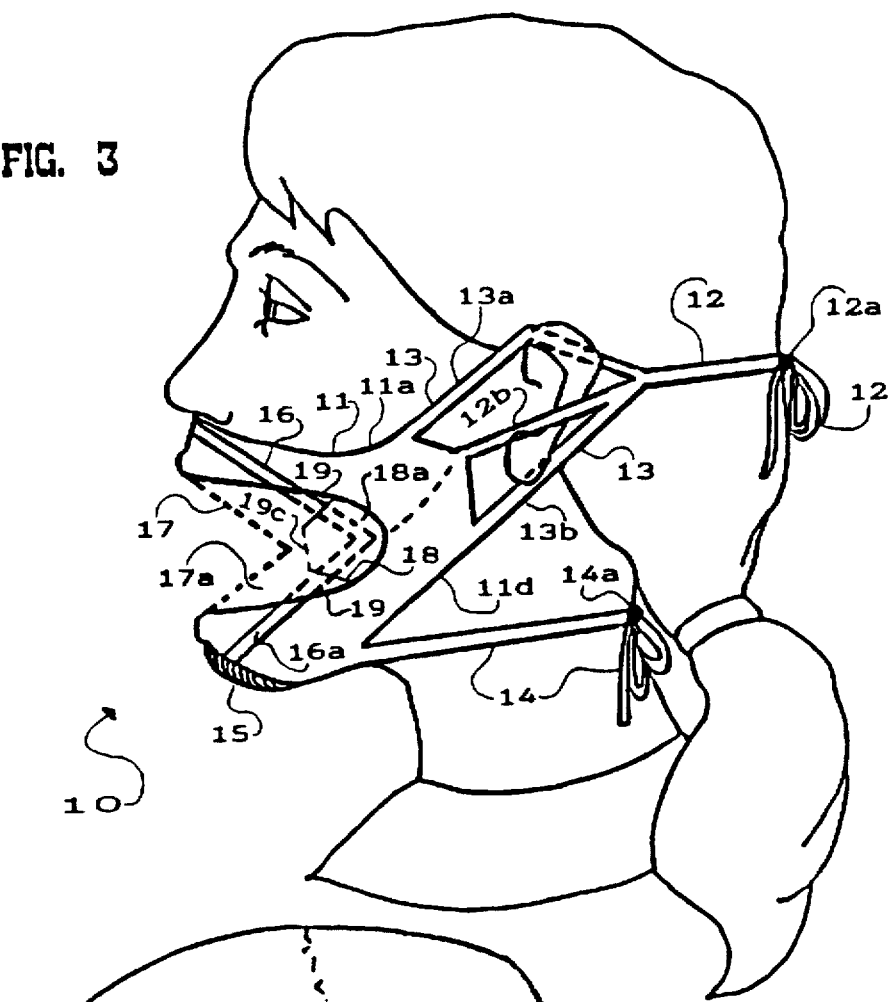
FIG. 3 is a left side-view of the protective mask, with the oral cavity and webs in the wide opened position and with the reversible flaccid pouch in front of and on the inside of the oral cavity.
Figure 3A:
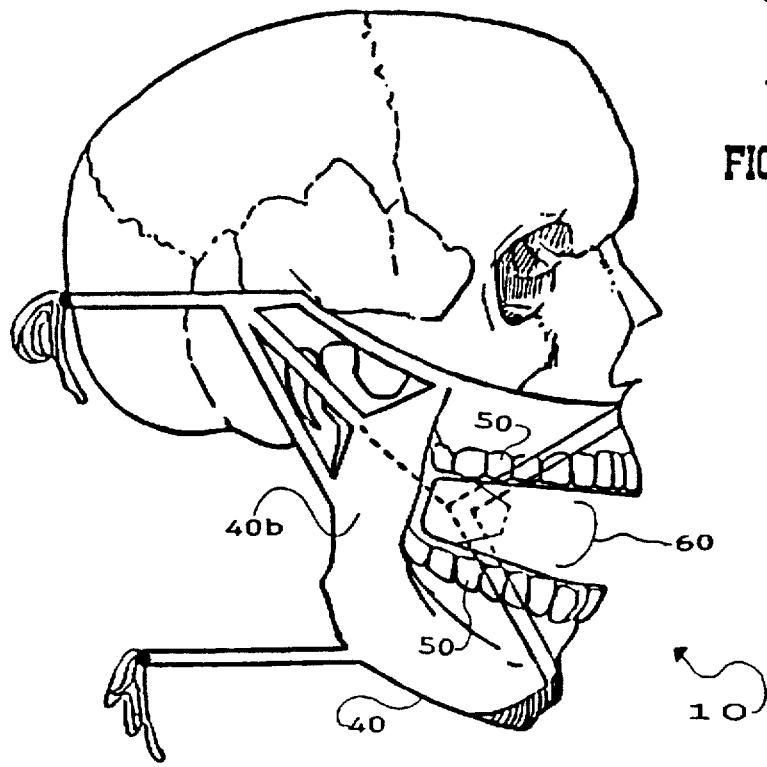
FIG. 3A is a right side-view of the protective mask indicating the position of the mandible when the oral cavity and webs are in the wide opened position and with the reversible flaccid pouch in front of and on the inside of the oral cavity.
Figure 4:
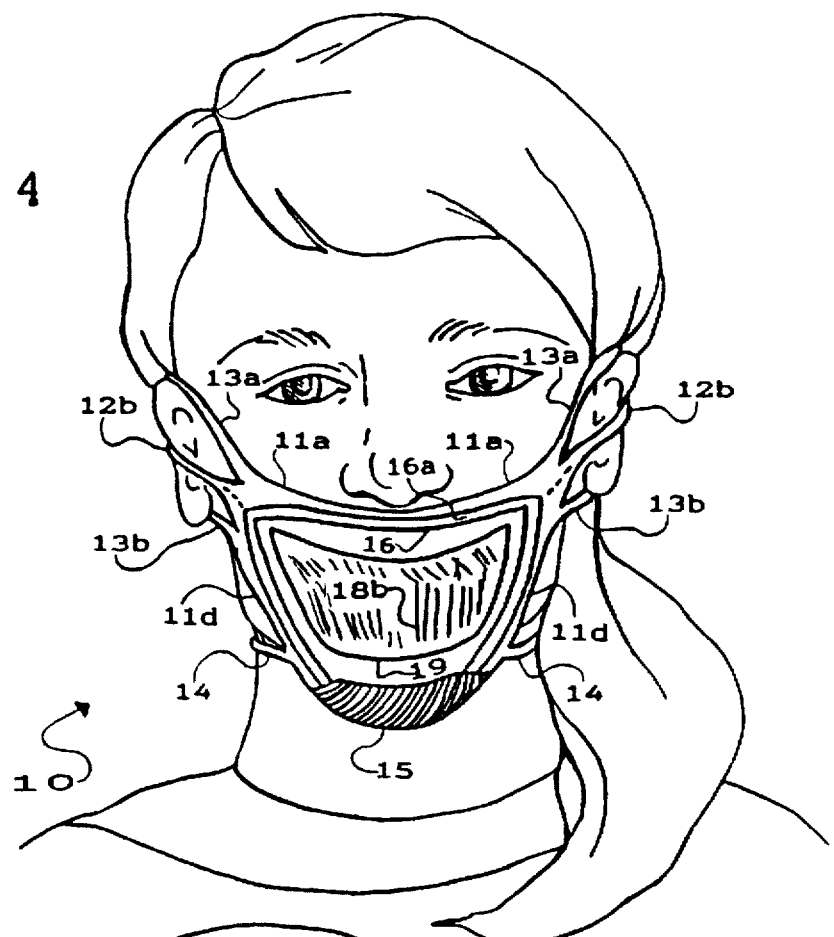
FIG. 4 is a frontal-view of the protective mask, with the oral cavity and webs in the wide opened position and with the reversible flaccid pouch and oral cavity receptors inside of the oral cavity.
Figure 4A:
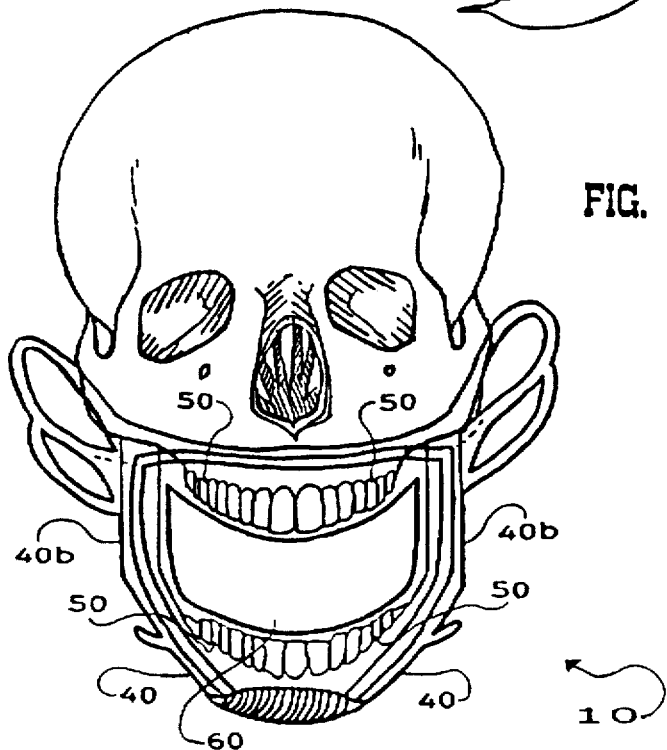
FIG. 4A is a frontal-view of the protective mask indicating the position of the mandible when the oral cavity and webs are in the wide opened position and with the reversible flaccid pouch in front of and on the inside of the oral cavity.
Figure 5:
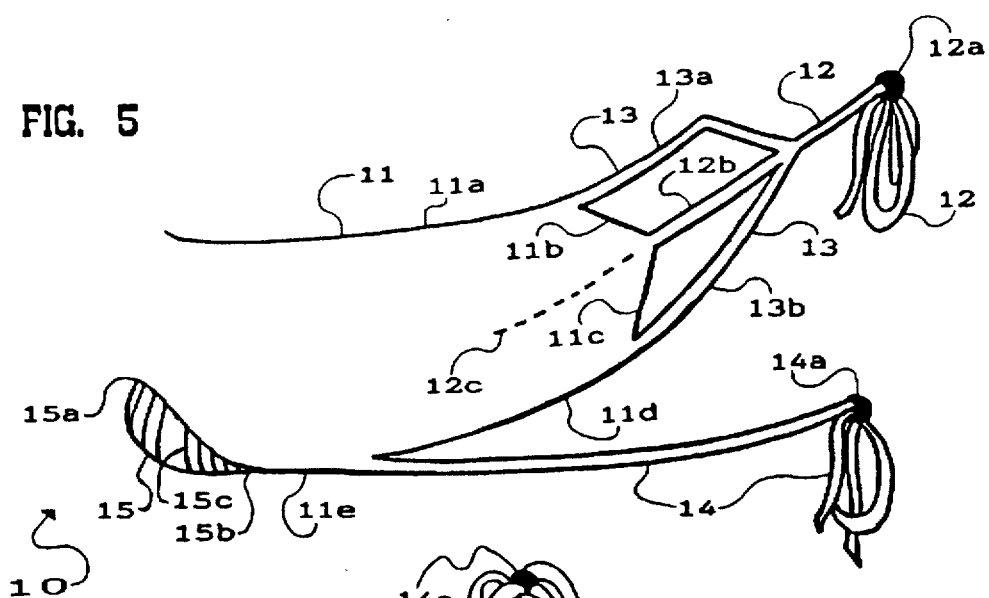
FIG. 5 is an isolated left side-view of the protective mask indicating the outlined boundaries, top and bottom pairs of primary film strings, top pairs of secondary film strings, the well-defined chin guard and the chin guard receptors.

The reversible half-oval shaped flaccid cavity pouch 19, as shown in FIG. 1, FIG. 1A, and FIG. 8, when closed, is a medium size half-oval shaped component which is located in front of the wearer's oral cavity 60. The flaccid pouch begins at 19a, which is directly under the nose bone 30b and covers some of the wearer's maxilla 30c. The flaccid pouch 19 ends at 19b near the mental foramen 40a. The oral cavity web 18 is in the 30 approximate center of the pouch 19.

B. Operation

The flaccid oral cavity pouch 19 is a reversible half-oval shaped component that, with the help of the oral cavity web 18 and the extra film pleat or groove 18a, can increase it's size from a medium half-oval shaped component to a large half circular shaped component without displacing the top portion 11a of the outlined boundary 11 of the mask 10 as shown in FIG. 9. The flaccid pouch 19 and the oral cavity web 18 functions are to reduce the levels of stress in the front of the mask 10 when the oral cavity 60 opens wide and to protect and operate in harmony and sequence with the outside of the oral cavity of the wearer as indicated in FIGS. 1, 1A, 2, 2A, 8, 9, and 11, and the inside of the oral cavity of the wearer as indicated in FIGS. 3, 3A, 4, 4A, 10, and 14 during employment.

VI. CONCLUSION, RAMIFICATIONS, and SCOPE of INVENTION

As the reader has comprehended from the previous description and the accompanying drawings, the protective mask of this invention is the omnibus 20 of protective masks. Not only is it versatile, it is also an economically disposable protective mask which can be employed by both males and females.

When the mask is being worn below the nose of the wearer, the primary (12 and 14) and secondary (13) film strings, outlined boundary (11), well-defined chin guard (15), jaw webs (16), cheek webs (17), oral cavity web (18), and the reversible half-oval shaped flaccid cavity pouch (19) all work together to allow the wearer of this versatile disposable film protective mask (10) to safely perform the many human oral sex-related functions.

Figure 11:
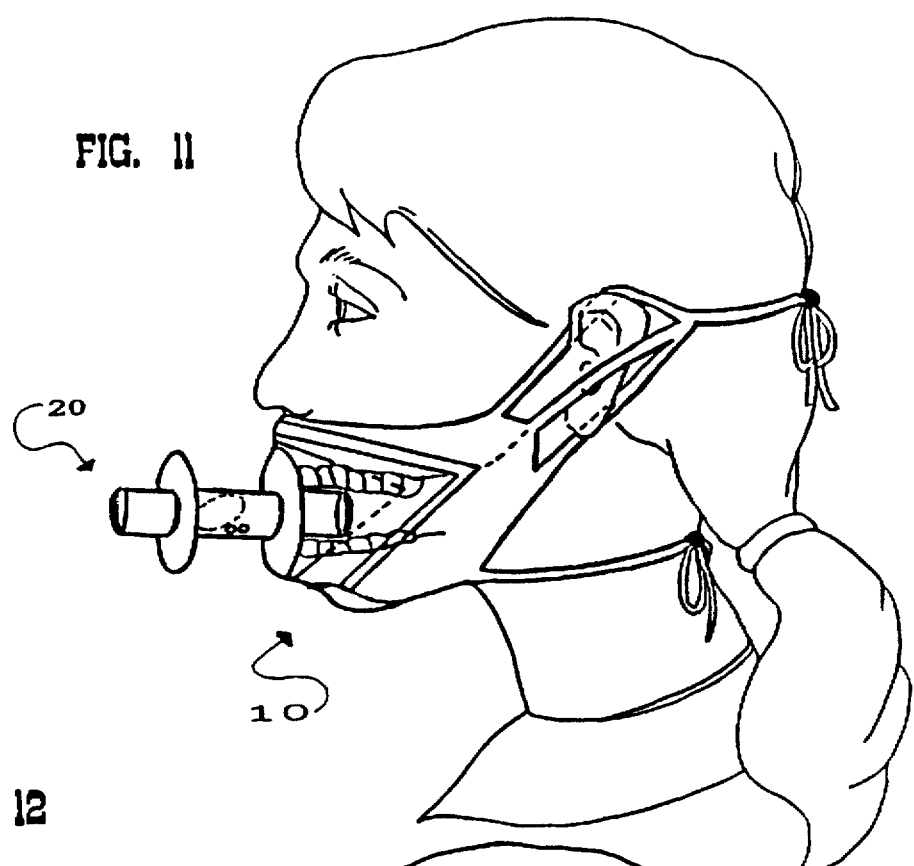
FIG. 11 is a left side-view of the protective mask when being employed as a resuscitation mask. The flaccid pouch is inserted with the one-way valve breathing tube with two disks on the tube shown in FIG. 12.
Figure 12:
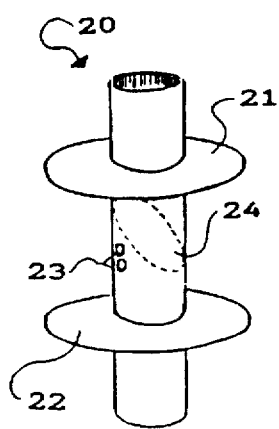
FIG. 12 is a side-view of the one-way valve breathing tube with two disks on the tube.
Figure 13:
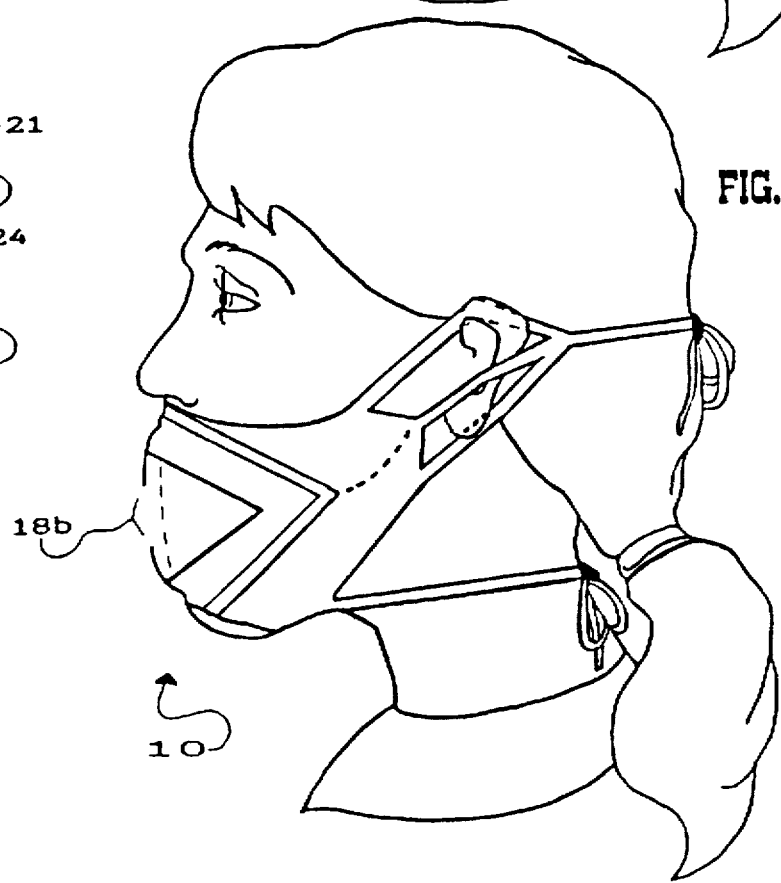
FIG. 13 is a left side-view of the protective mask after the one-way breathing tube with two disks has been inserted in a hole in the oral cavity web and flaccid pouch.

Furthermore, this protective mask will simplify the process for covering and protecting the outside and inside of the oral cavity when the mask is being employed to perform the following functions:

1. Resuscitation mask (FIG. 11)

Figure 11A:
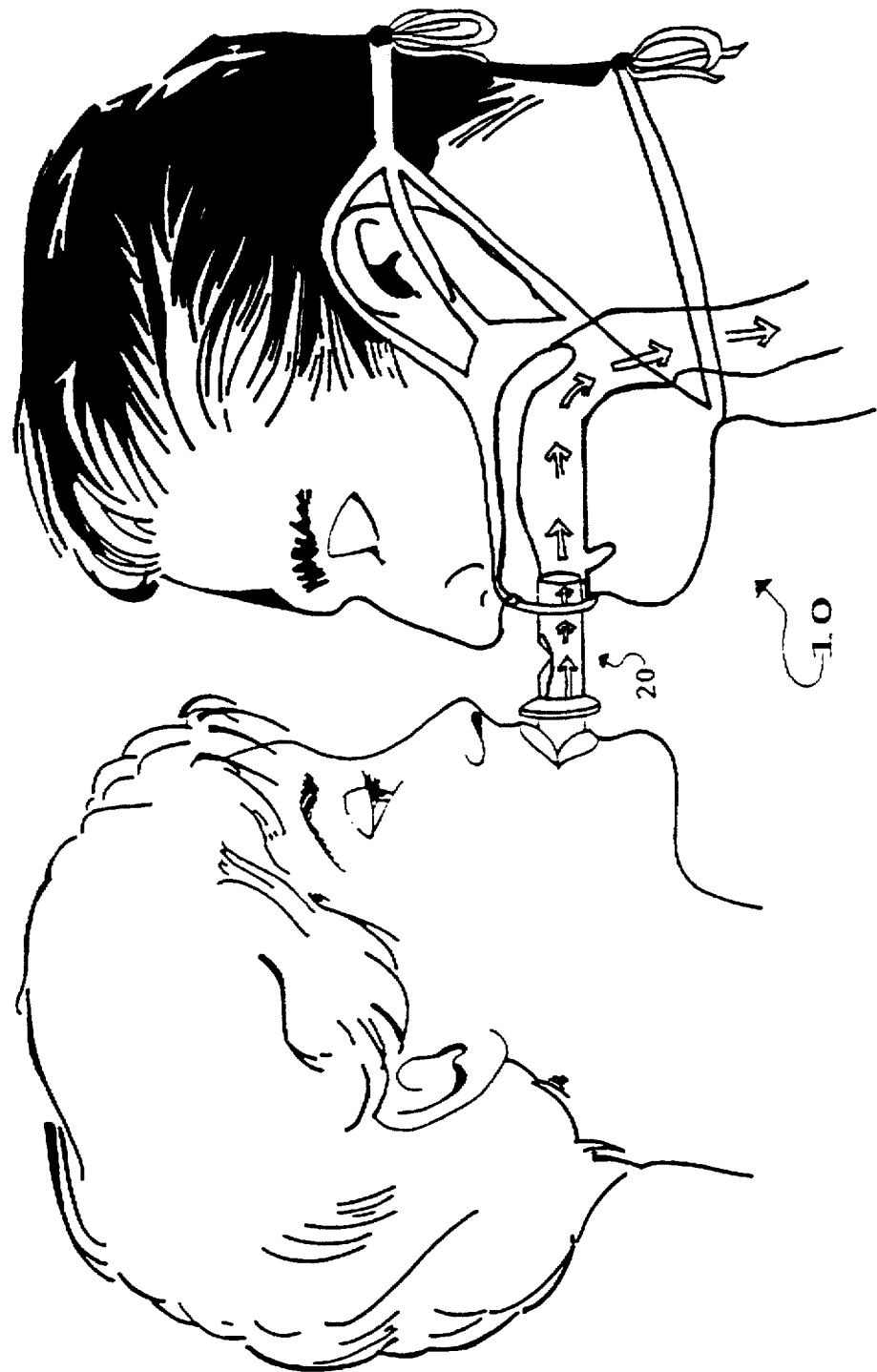
FIG. 11A is a left-side view application of the mask when worn below the nose during mouth-to-mouth resuscitation.

The protective mask 10 may be employed as a mouth-to-mouth resuscitation mask (FIG. 11A). The flaccid pouch 19 is inserted by the one-way valve breathing tube 20 with one disk on each end of the tube (FIG. 11A).

2. Dental Dam (FIG. 14)

Figure 14:
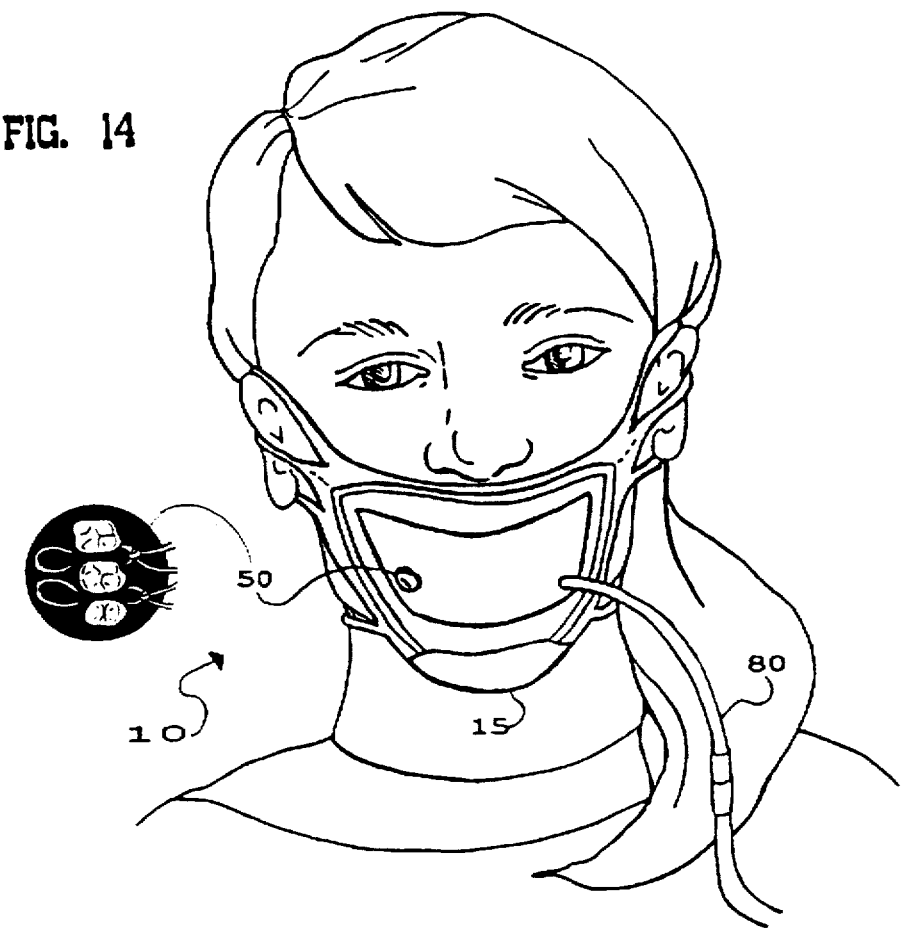
FIG. 14 is a frontal-view of the protective mask being employed as a dental dam to isolate a damaged tooth.

The protective mask 10 may be employed by dentists to isolate and repair damaged teeth (FIG. 14). Currently, dentists are using a dental dam to cover and protect the outside and inside of the oral cavity when repairing damaged teeth. A pouch is formed inside the oral cavity by clamping the center of the square piece of latex to the back teeth. Then, a large plastic or metal frame is placed in front of the face and the oral cavity. Next, the sides and corners are pulled forward and outward and mounted on the sides of the plastic or metal frame to hold the sides and corners of the square piece of latex in place and to secure the dental dam on the lower face of the wearer. This is a complicated procedure. One of the many functions of this protective mask is to replace the current dental dam, the plastic frame, and the metal frame.

This protective mask is designed and constructed with a reversible half-oval shaped flaccid cavity pouch 19 with an oral cavity web 18 between it that conforms to the outside and inside of the oral cavity. In addition, the body of this protective mask has two sets of webs (jaw webs 16 and cheek webs 17) that will operate in harmony and sequence with the mandible 40 allowing the dentist to open the wearer's oral cavity 60 as wide as necessary. In addition, this protective mask has a top pair 12 and bottom pair 14 of primary film strings to secure the mask 10 on the wearer's face, making it easier for the dentist to put the mask 10 on and take it off of the wearer's face. The reversible flaccid cavity pouch 19 of this protective mask 10 is compatible with the current equipment used to mark, clamp and hold a conventional dental dam inside the oral cavity 60.

While the above descriptions and/or operations contain many specificities, these should not be construed as limitations on the scope of the invention, but rather as exemplifications of the preferred embodiments thereof. Clearly, many other variations are possible. For example, when the mask 10 is worn below the waist of the wearer, being employed as a male or female G-string flaccid pouch (FIG. 15 or FIG. 18), the mask 10 will be turned upside down and the well-defined chin guard 15 will be flattened out. The two pairs of secondary film strings/ear loops 13 would then be enlarged so that a person's legs will fit between them. The two pairs of primary film strings 12 and 14 would then be employed to properly pull back, stabilize, and secure the mask 10 against the wearer's lower body.

Figure 15:
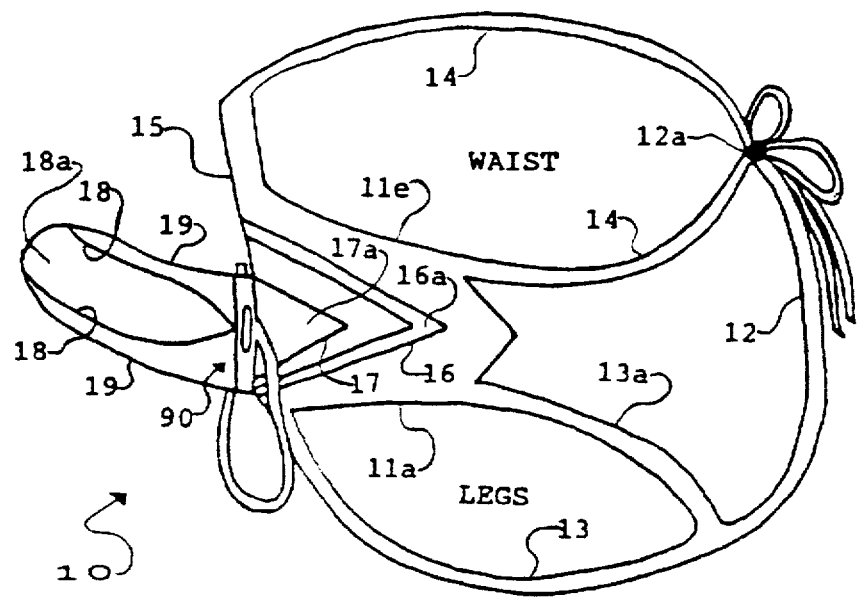
FIG. 15 is a left side-view of the protective mask being employed as a male G-string flaccid pouch.

3. Male G-string flaccid pouch (FIG. 15)

When the mask is employed as a male G-string flaccid pouch (FIG. 15), it will have a male disposable film flaccid pouch harness 90 (FIG. 16), which is a device constructed of two wide connecting bands 91 and 95 consisting of latex, polyurethane, and/or rubber provided for securing the flaccid pouch 19. The first wide band 91 has a circular configuration and the second wide band 95 has an oblong configuration that connects to the approximate center of the first wide band 91. This second wide band 95, is a safety band to secure the first band 95 to the wearer.

The first band 91, in addition to the second band 92, of the male disposable film flaccid pouch harness 90 (FIG. 16) has three small half circular bands/handles protruding from it. The left side center applicator handle 93 and the right side center applicator handle 94 are used to prevent ripping or tearing the flaccid pouch when applying the first band 91 of the flaccid pouch harness 90 and the flaccid pouch 19. The top center handle 96 is used to release trapped air inside the flaccid pouch 19, by pulling upward on it to release the trapped air, before the male G-string flaccid pouch (FIG. 15) is used for its intended purpose.

Figure 16:
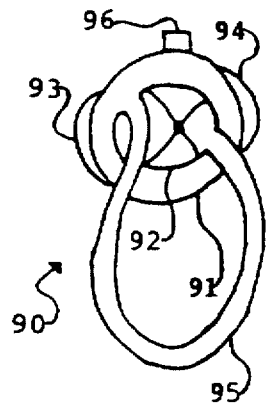
FIG. 16 is a male disposable film flaccid pouch harness, that can be constructed with the male G-string flaccid pouch or independent of it.
Figure 17:
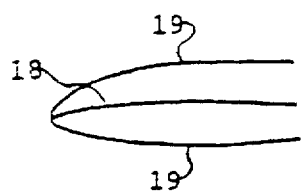
FIG. 17 is a union of the flaccid pouch and the male G-string flaccid pouch harness.
Figure 17:
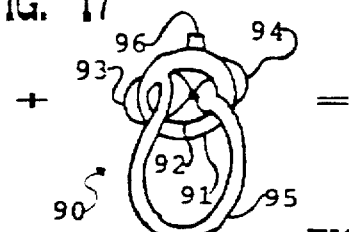
Figure 17A:
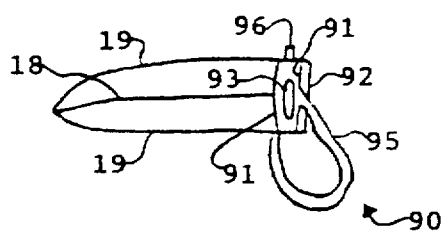
FIG. 17A is a male flaccid pouch with an uncontained flaccid pouch, wherein the oral cavity web seal is unbroken in the closed position.
Figure 17B:
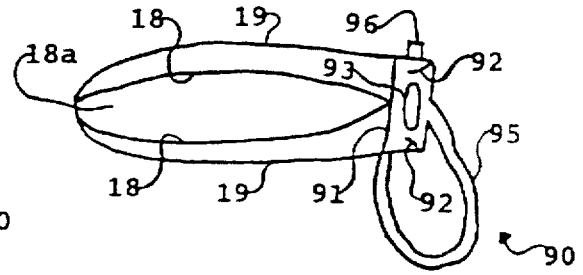
FIG. 17B is the flaccid pouch of FIG. 17A with the rear thin breakable seal and front thin breakable seal broken to release a lubricant and with the oral cavity web thin breakable seal broken to reveal the extra film between the oral cavity web, which likewise releases a lubricant.

The isolated view of the male G-string flaccid pouch is FIG. 17, the union of the flaccid pouch 19 (FIG. 15) and the male G-string flaccid pouch harness 90 (FIG. 16). FIG. 17A is a male flaccid pouch with an uncontained flaccid pouch 19, with the oral cavity web seal 18 unbroken in the closed position. FIG. 17B is a male flaccid pouch 19 with the rear thin seal 92 broken to release a lubricant, and the oral cavity web seal 18 broken to reveal the extra film between the oral cavity web 18a, to increase the width and length of the flaccid pouch 19 and to release a lubricant.

Figure 18:
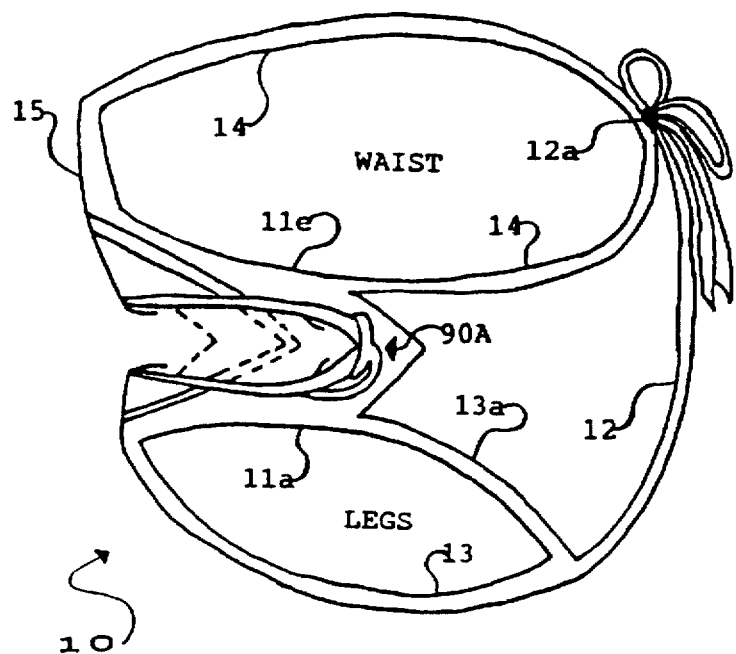
FIG. 18 is a left side-view of the protective mask being employed as a female G-string flaccid pouch.

4. Female G-string Flaccid Pouch (FIG. 18)

Figure 18A:
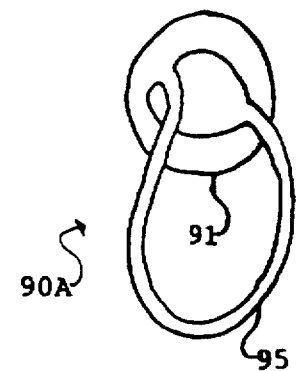
FIG. 18A is a female disposable film flaccid pouch harness that can be constructed with the female G-string flaccid pouch or independent of it.

When the mask is employed as a female G-string flaccid pouch (FIG. 18), the female disposable film flaccid pouch harness 90a, (FIG. 18A), is employed for securing the flaccid pouch 19 on the wearer. The first wide band 91 is positioned in front of the flaccid pouch 19. When the flaccid pouch 19 is employed, the front of the flaccid pouch 19 will cover and protect the cervix. The first wide band 91 secures the flaccid pouch 19 during use and the second band 95 is used to remove the flaccid pouch 19 after use.

This versatile disposable film protective mask 10 is also available in twelve or more flavors, colors, prints, and pattern designs to make it more marketable. Further, the flaccid pouch 19 may have two oral cavity webs 18, one horizontal and the other vertical. Both pleated folds of extra film material 18a of the oral cavity webs 18 may contain a lubricant in them to make the reversible oval shaped flaccid cavity pouch 19 self-lubricating. The chin guard may also have one or more sacks, which contain a lubricant, attached to it with one or more flexible perforated tubes extending onto the outside and inside of the flaccid pouch and oral cavity web(s). When pressed the sack(s) will provide additional lubricant, if needed, to the flaccid pouch and oral cavity web(s). In addition, the chin guard 15 may have human or synthetic hair applied to it for a more natural look and feel. Accordingly, the scope of the invention should not only be determined by the embodiments illustrated and described herein, but also by the appended claims and their legal equivalents.

I claim:

1. A protective mask for providing an impermeable barrier to a liquid virus, said mask comprising a generally planar body portion made of a thin, elastic first film material, said body portion having an interior surface, an exterior surface and an outer periphery defined by an upper boundary, a lower boundary and a pair of opposed side boundaries connecting said upper boundary and said lower boundary, said body portion comprising a bottom portion formed by a plurality of folded pleats of the first film material, said bottom portion positioned adjacent said lower boundary and shaped to conform to the contour of a human being's chin;

a jaw web formed by at least one folded pleat of the first film material, said jaw web defining an acute angle extending between said upper boundary and said lower boundary; and a flaccid cavity pouch positioned medially between said upper boundary and said lower boundary opposite said jaw web.

2. A protective mask according to claim 1 wherein said flaccid cavity pouch extends between said upper boundary and said bottom portion.

3. A protective mask according to claim 1 wherein said flaccid cavity pouch comprises a cheek web formed by at least one folded pleat of the first film material, said cheek web positioned within the acute angle defined by said jaw web; and an oral cavity web formed by at least one folded pleat of the first film material, said oral cavity web positioned within the acute angle defined by said jaw web adjacent said cheek web.

4. A protective mask according to claim 3 wherein said flaccid cavity pouch is half oval shaped and wherein said cheek web and said oral cavity web are generally linear.

5. A protective mask according to claim 4 wherein said oral cavity web is generally parallel to said cheek web.

6. A protective mask according to claim 1 further comprising a pair of top securing strings extending outwardly from said upper boundary of said body portion for securing the protective mask to a human being; and a pair of bottom securing strings extending outwardly from said lower boundary of said body portion for securing the protective mask to a human being.

7. A protective mask according to claim 6 wherein each of said pair of top securing strings comprises a primary securing string and a pair of secondary securing strings, said primary securing string positioned medially between said pair of secondary securing strings.

8. A protective mask according to claim 6 wherein each of said pair of top securing strings and each of said pair of bottom securing strings is made of a thin, elastic second film material that is less elastic than the first film material.

9. A protective mask according to claim 1 wherein the first film material is selected from the group consisting of liquid latex and liquid polyurethane.

10. A protective mask according to claim 6 wherein the first film material is selected from the group consisting of liquid latex and liquid polyurethane.

11. A protective mask according to claim 1 further comprising a generally planar, thin lining for absorbing liquid that is capable of containing the liquid virus, said lining having an adhesive layer applied to a surface thereof for adhering said lining to the interior surface of said body portion.

12. A protective mask according to claim 11 wherein said lining is sized to be positioned within the outer periphery of said body portion and comprises a plurality of contoured portions corresponding in position and shape to each of said bottom portion, said jaw web and said flaccid cavity pouch.

13. A protective mask according to claim 1 further comprising a flaccid cavity pouch harness for securing said flaccid cavity pouch to a human being's genitals.

14. A protective mask according to claim 13 wherein said flaccid cavity pouch harness comprises at least one semi-circular band protruding outwardly therefrom for applying said flaccid cavity pouch and said flaccid cavity pouch harness to the human being's genitals.

15. A protective mask according to claim 1 wherein said flaccid cavity pouch is reversible so that said mask may be used by a male human being or a female human being.

16. A protective mask according to claim 1 wherein the plurality of folded pleats of said bottom portion are coated with a lubricant.

17. A protective mask according to claim 2 wherein the at least one folded pleat of said oral cavity web is coated with a lubricant.

18. A protective mask for providing an impermeable barrier to a liquid virus, said mask comprising a generally planar body portion made of a thin, elastic first film material, said body portion having an interior surface, an exterior surface and an outer periphery defined by an upper boundary, a lower boundary and a pair of opposed side boundaries connecting said upper boundary and said lower boundary, said body portion comprising a bottom portion formed by a plurality of folded pleats of the first film material, said bottom portion positioned adjacent said lower boundary and shaped to conform to the contour of a human being's chin;

a jaw web formed by at least one folded pleat of the first film material, said jaw web defining an acute angle extending between said upper boundary and said lower boundary; and a half oval shaped flaccid cavity pouch extending between said upper boundary and said bottom portion and positioned opposite said jaw web, said flaccid cavity pouch comprising a generally linear cheek web formed by at least one folded pleat of the first film material; and a generally linear oral cavity web formed by at least one folded pleat of the first film material, said oral cavity web positioned generally parallel to and adjacent said cheek web;

a pair of top securing strings made of a thin, elastic second film material that is less elastic than the first film material, said pair of top securing strings extending outwardly from said upper boundary of said body portion for securing the protective mask to a human being;

a pair of bottom securing strings made of the thin, elastic second film material, said pair of bottom securing strings extending outwardly from said lower boundary of said body portion for securing the protective mask to a human being; and a generally planar, thin lining for absorbing liquid that is capable of containing the liquid virus, said lining having an adhesive layer applied to a surface thereof for adhering said lining to the interior surface of said body portion, said lining sized to be positioned within the outer periphery of said body portion and comprising a plurality of contoured portions corresponding in position and shape to each of said bottom portion, said jaw web and said flaccid cavity pouch.

\* \* \* \* \*